_{US005543151A}_

United States Patent [19]

Shirai et al.

[11] Patent Number: 5,543,151
[45] Date of Patent: Aug. 6, 1996

[54] MEDICAL PRESSURE-SENSITIVE ADHESIVE AND MEDICAL BANDAGE FORMED USING THE SAME

[75] Inventors: Fumiya Shirai; Masayoshi Kuniya; Chiemi Mikura; Tomoko Matsushita; Hitoshi Akemi; Toshiyuki Yamamoto, all of Osaka, Japan

[73] Assignee: Nitto Denko Corporation, Osaka, Japan

[21] Appl. No.: 237,990

[22] Filed: May 4, 1994

[30] Foreign Application Priority Data

May 11, 1993 [JP] Japan .................................. 5-133994

[51] Int. Cl.⁶ ......................................................... A61F 13/00
[52] U.S. Cl. ......................... 424/448; 424/447; 424/449
[58] Field of Search .................................... 424/448, 449, 424/447

[56] References Cited

U.S. PATENT DOCUMENTS

| 4,751,087 | 6/1988 | Wick | 424/449 |
| 4,994,267 | 2/1991 | Sablotsky | 424/78 |

*Primary Examiner*—D. Garbrielle Phelan
*Attorney, Agent, or Firm*—Sughrue, Mion, Zinn, Macpeak & Seas

[57] ABSTRACT

A medical pressure-sensitive adhesive and a medical bandage formed using the same are disclosed. The medical pressure-sensitive adhesive comprises an acrylic polymer and a specific liquid or pasty component which is in a liquid state or pasty state at room temparature and is compatible with the acrylic polymer. The medical pressure-sensitive adhesive is suitable for use as a plaster, a pressure-sensitive dressing, a poultice and the like.

7 Claims, No Drawings

MEDICAL PRESSURE-SENSITIVE ADHESIVE AND MEDICAL BANDAGE FORMED USING THE SAME

FIELD OF THE INVENTION

The present invention relates to a medical pressure-sensitive adhesive which is suitably used for a plaster, a pressure-sensitive dressing, a poultice, etc., and to a medical bandage formed using the pressure-sensitive adhesive.

BACKGROUND OF THE INVENTION

Hitherto, various kinds of medical pressure-sensitive adhesives have been used for medical bandages.

As the result of attaching importance to the adhesion to the skin in conventional medical pressure-sensitive adhesives, the countermeasures to the skin stimulation has been insufficient.

Recently, since percutaneous absorption-type preparations prepared by incorporating a drug or drugs in pressure-sensitive adhesives are increased and the adhering time is prolonged, the countermeasures to the skin stimulation become necessary, and many medical pressure-sensitive adhesives prepared by compounding a polymer with a large amount of a liquid or pasty component having a good compatibility with the polymer and giving very slight damage to a stratum corneum have been proposed as one of such countermeasures.

However, some of these medical pressure-sensitive adhesives are used for the skin only as adhesives containing drugs and others are applied in various states for various medical fittings and medical instruments, such as a means for fixing catheters, etc.

For some of such medical fittings and medical instruments, a material into which a plasticizer is easily transferred, such as non-plasticized polyvinyl chloride, is used and when a medical pressure-sensitive adhesive containing a liquid or pasty component is applied to such a medical fitting or medical instrument, the liquid or pasty component is easily transferred into the medical fitting or the medical instrument to cause a possibility of damaging the medical fitting or the medical instrument.

Further, when a medical bandage is prepared by forming the layer of the pressure-sensitive adhesive on a support, the liquid or pasty component is transferred into the support to change the composition of the medical pressure-sensitive adhesive. Thus, in spite of the disadvantage that it is necessary to use a support into which such a liquid or pasty component of the medical pressure-sensitive adhesive is not transferred, which results in greatly restricting the selective range of the support, any investigation has not been made at present from this point on the medical pressure-sensitive adhesive compounded with a large amount of a liquid or pasty component.

SUMMARY OF THE INVENTION

As a result of investigations to overcome the above-described technical problems involved in the prior art, it has now been found that a medical pressure-sensitive adhesive which is a specific pressure-sensitive adhesive comprising an acrylic polymer as the main component which is crosslinked at a definite ratio has a good adhesive property to the skin, does not almost give a skin stimulation, and is very slight to damage to a stratum corneum. It has also been found that when the pressure-sensitive adhesive is applied to medical fittings or medical instruments which use a material into which a plasticizer is liable to transfer, such as non-plasticized polyvinyl chloride, the pressure-sensitive adhesive does not damage the fittings or the instruments and further since a liquid or pasty component in the pressure-sensitive adhesive does not transfer into a support of the pressure-sensitive adhesive, the selective range of the support can be enlarged.

Accordingly, one object of the present invention is to provide a medical pressure-sensitive adhesive suitably used for a plaster, a pressure-sensitive dressing, a poultice, etc.

Another object of the present invention is to provide a medical bandage formed by using the pressure-sensitive adhesive.

The medical pressure-sensitive adhesive according to the present invention comprises 100 parts by weight of an acrylic polymer and from 30 to 100 parts by weight of a component which is in a liquid state or a pasty state at room temperature and is compatible with the acrylic polymer, wherein the liquid or pasty component is at least one ester selected from the group consisting of an ester of a monobasic acid or a polybasic acid each having from 8 to 18 carbon atom and a branched alcohol having from 14 to 18 carbon atoms, and an ester of an unsaturated fatty acid or a branched acid each having from 14 to 18 carbon atoms and a tetrahydric or lower hydric alcohol, and from 40 to 80% by weight of the acrylic polymer is insolubilized by crosslinking.

DETAILED DESCRIPTION OF THE INVENTION

The present invention is described in detail below.

The acrylic polymer used in the present invention is a polymer or a copolymer comprising a (meth)acrylic acid ester as the main component, if necessary, copolymerized with a monomer copolymerizable with the (meth)acrylic acid ester.

Example of the (meth)acrylic acid ester is a (meth)acrylic acid alkyl ester having at least 2 carbon atoms, and preferably 15 or less carbon atoms, in the alkyl moiety. Specific examples thereof are (meth)acrylic acid alkyl esters each having a straight chain or branched alkyl group, such as ethyl (meth)acrylate, n-butyl (meth)acrylate, isobutyl (meth)acrylate, pentyl (meth)acrylate, hexyl (meth)acrylate, heptyl (meth)acrylate, octyl (meth)acrylate, isooctyl (meth) acrylate, 2-ethylhexyl (meth)acrylate, nonyl (meth)acrylate, isononyl (meth)acrylate, decyl (meth)acrylate, undecyl (meth)acrylate, tridecyl (meth)acrylate, etc.

Those (meth)acrylic acid esters can be used alone or as mixtures thereof.

Examples of the monomer copolymerizable with the (meth)acrylic acid alkyl ester are carboxyl group-containing monomers such as (meth)acrylic acid, itaconic acid, maleic acid, maleic anhydride, etc.; sulfoxyl group-containing monomers such as styrenesulfonic acid, allylsulfonic acid, sulfopropyl (meth)acrylate, (meth)acryloyloxynaphthalenesulfonic acid, acrylamidomethylpropanesulfonic acid, etc.; hydroxyl group-containing monomers such as (meth)acrylic acid hydroxyethyl ester, (meth)acrylic acid hydroxypropyl ester, etc.; amido group-containing monomers such as (meth)acrylamide, dimethyl(meth)acrylamide, N-butylacrylamide, N-methylol-(meth)acrylamide, N-methylolpropane(meth)acrylamide, etc.; alkylaminoalkyl group-containing monomers such as (meth)acrylic acid aminoethyl ester, (meth)acrylic acid dimethylaminoethyl ester, (meth)acrylic acid tert-butylaminoethyl ester, etc.; (meth)acrylic acid alkoxyalkyl esters such as (meth)acrylic acid methoxyethyl ester, (meth)acrylic acid ethoxyethyl ester, etc.; alkoxy group (or ether bond at the side chain)-containing (meth) acrylic esters such as (meth)acrylic acid methoxyethylene glycol ester, (meth)acrylic acid tetrahydrofurfuryl ester, (meth)acrylic acid methoxyethylene glycol ester, (meth) acrylic acid methoxydiethylene glycol ester, (meth)acrylic acid methoxypolyethylene glycol ester, (meth)-acrylic acid methoxypropylene glycol ester, etc.; and vinyl monomers such as (meth)acrylonitrile, vinyl acetate, vinyl propionate, N-vinyl-2-pyrrolidone, methylvinylpyrrolidone, vinylpyridine, vinylpiperidine, vinylpyrimidine, vinylpiperazine, vinylpyrazine, vinylpyrrole, vinylimidazole, vinylcaprolactam, vinyloxazole, vinylmorpholine, etc.

Those monomers can Be used alone or as mixtures thereof.

Those monomers copolymerizable with the (meth)acrylic acid ester can be used to control the cohesive force of the pressure-sensitive adhesive layer and to improve the compatibility with the liquid or pasty component, and the copolymerization amount can be optionally selected according to the purpose of the pressure-sensitive adhesive.

Of the acrylic polymers described above, copolymers obtained by copolymerizing the (meth)acrylic acid alkyl ester with at least one kind of the carboxyl group-containing monomers and hydroxyl group-containing monomers described above as an essential component together with, if necessary, other monomer described above are preferably used in the present invention from the standpoints of controlling the degree of the crosslinking and controlling the adhesive properties.

The liquid or pasty component used in the present invention is compounded with the acrylic polymer to exhibit the characteristics that the modulus of the pressure-sensitive adhesive in the low deformation region thereof is decreased, a good adhesive property to the skin is maintained, and the damage of a stratus corneum and the pain at detaching the pressure-sensitive adhesive are decreased.

Accordingly, the liquid or pasty component used in the present invention must satisfy the characteristics that the component is in a liquid state or a pasty state at an actually using temperature (room temperature) and when the component is compounded with the acrylic polymer used in the present invention, the component shows a good compatibility with the acrylic polymer and is difficult to transfer into a medical fitting or a medical instrument, which is one of the main objects of the present invention.

The liquid or pasty component comprises at least one ester selected from the group consisting of an ester of a monobasic acid or a polybasic acid each having from 8 to 18 carbon atoms and a branched alcohol having from 14 to 18 carbon atoms, and an ester of an Unsaturated fatty acid or a branched acid each having from 14 to 18 carbon atoms and a tetrahydric or lower hydric alcohol.

Examples of the monobasic acid or the polybasic acid each having from 8 to 18 carbon atoms are lauric acid, myristic acid, palmitic acid, stearic acid, oleic acid, adipic acid, sebacic acid, trimellitic acid, etc.

Examples of the branched alcohol having from 14 to 18 carbon atoms are isostearyl alcohol, isocetyl alcohol, octyldodecyl alcohol, diisostearyl alcohol, diisocetyl alcohol, trioleyl alcohol, triisocetyl alcohol, etc.

Examples of the ester of the monobasic acid or the polybasic acid and the branched alcohol are isostearyl laurate, isocetyl myristate, octyldodecyl myristate, isostearyl palmitate, isocetyl stearate, octyldodecyl oleate, diisostearyl adipate, diisocetyl sebacate, trioleyl trimellitate, triisocetyl trimellitate, etc.

Examples of the unsaturated fatty acid or the branched acid each having from 14 to 18 carbon atoms are myristoleic acid, oleic acid, linoleic acid, linolenic acid, isopalimitic acid, isostearic acid, etc.

Examples of the tetrahydric or lower hydric alcohol are ethylene glycol, propylene glycol, glycerol, trimethylolpropane, pentaerythritol, sorbitan, etc.

Example of the ester of the unsaturated fatty acid or a branched acid each having from 14 to 18 carbon atoms and a tetrahydric or lower hydric alcohol are sorbitan trioleate, trimethylolpropane triisostearate, glycerol triisostearate, etc.

The reason for using the ester of the monobasic acid or polybasic acid each having from 8 to 18 carbon atoms and the branched alcohol having from 14 to 18 carbon atoms in the present invention is as follows.

If the carbon atom number of the monobasic acid or the polybasic acid is less than 8, the transfer property of the liquid or pasty component into medical fittings or medical instruments is undesirably increased and on the other hand, if the carbon atom number thereof is over 18, the compatibility of the liquid or pasty component with the acrylic polymer is undesirably reduced, whereby good adhesive characteristics are not obtained.

Even when the monobasic acid or the polybasic acid each having from 8 to 18 carbon atoms is used for the liquid or pasty component used in the present invention, if the carbon atom number of the branched alcohol used for the component is less than 14 and the component is in a liquid state at room temperature, the component is easily transferred into a material into which a plasticizer is liable to transfer, such as non-plasticized polyvinyl chloride, and on the other hand, if the carbon atom number of the branched alcohol is over 18, the compatibility of the component with the acrylic polymer is reduced. Thus, both the cases are undesirable.

Further, when the liquid or pasty component used in the present invention comprises the ester of the unsaturated fatty acid or the branched acid and the polyhydric (tetrahydric or lower hydric) alcohol, if the carbon atom number of the unsaturated fatty acid or the branched acid is less than 14 and the component is in a liquid state at room temperature, the component is easily transferred into a material into which a plasticizer is liable to transfer and on the other hand, if the carbon atom number of the unsaturated fatty acid or the branched acid is over 18, the compatibility of the component with the acrylic polymer is reduced. Thus, both the cases are also undesirable.

In the present invention, from 30 to 100 parts by weight, and preferably from 30 to 80 parts by weight of at least one kind of the liquid or pasty component is incorporated in 100 parts by weight of the acrylic polymer.

In this case, the uncrosslinked acrylic polymer is used and after compounding the acrylic polymer with the liquid or pasty component, the acrylic polymer is subjected to a crosslinking treatment such that from 40 to 80% by weight of the acrylic polymer becomes insoluble.

By applying the crosslinking treatment to the acrylic polymer as described above, the improvement of the cohesive force of the pressure-sensitive adhesive and a proper adhesion can be obtained.

The crosslinking treatment which can be employed in the present invention is a physical treatment such as a x-ray irradiation, an electron ray irradiation, etc., and a chemical crosslinking treatment with an organic peroxide, an isocyanate compound, an organic metal salt, a metal alcoholate, a metal chelate compound, an epoxy group-containing compound, a primary amino group-containing compound, etc. The isocyanate compound, the metal alcoholate compound, or the metal chelate compound is suitably used as the compound for the chemical crosslinking treatment from the points of the easiness of compounding the components for the pressure-sensitive adhesive (excellent storage stability until adding a crosslinking agent to the pressure-sensitive adhesive and coating the same; i.e., a long pot-life) and controlling the degree of crosslinking.

In this case, the amount of the crosslinking agent used is controlled such that from 40 to 80% by weight of the acrylic polymer is insolubilized.

If the percentage of the insolubilization is less than 40% by weight of the acrylic polymer, the cohesive force of the pressure-sensitive adhesive of the present invention is insufficient, whereby there are possibilities that the pressure-sensitive adhesive remains on the skin and the adhesive oozes from the side of a plaster and where a porous support such as a nonwoven fabric is used, a phenomenon occurs that the pressure-sensitive adhesive passes through the support. On the other hand, if the percentage of the insolubilization is over 80%, a sufficient adhesion to the skin is not obtained.

The liquid or pasty component used in the present-invention includes a component containing an unsaturated double bond, and when such a component is used, it is preferred to use an antioxidant for stabilizing the component.

The medical pressure-sensitive adhesive of the present invention is formed on at least one surface of a support to obtain the medical bandage of the present invention.

In more detail, the medical bandage of the present invention is prepared by directly coating the medical pressure-sensitive adhesive on one surface or both surfaces of a support followed by drying, or by coating the pressure-sensitive adhesive on a releasing paper followed by drying and adhering the releasing paper having the pressure-sensitive adhesive layer to a support such that the pressure-sensitive adhesive layer faces the support.

In the present invention, the uncrosslinked acrylic polymer is compounded with the liquid or pasty component which is in a liquid state at room temperature and is compatible with the acrylic polymer in the above-described proportion, and the resulting mixture is directly coated on one surface or both surfaces of a support followed by drying, or the resulting mixture is coated on a releasing paper followed by drying and the releasing paper having the pressure-sensitive adhesive layer is adhered to a support. The layer of the pressure-sensitive adhesive is subjected to a crosslinking treatment by the method described above such that from 40 to 80% by weight of the uncrosslinked acrylic polymer becomes insoluble.

The crosslinking treatment can be properly selected from the crosslinking methods described above.

There is no particular restriction on the support used in the present invention if the support can support thereon the layer or layers of the medical pressure-sensitive adhesive, and a film-form or sheet-form support Which is usually used for plasters, pressure-sensitive dressings, poultices, etc., can be used. The support may be porous or non-porous.

The medical pressure-sensitive adhesive of the present invention is the pressure-sensitive adhesive having the above-described construction and comprising the acrylic polymer and the specific liquid or pasty ester. The acrylic polymer is crosslinked in a predetermined proportion, whereby the pressure-sensitive adhesive has a good adhesive property to the skin, does not substantially show a skin stimulation, is safe with very slight damage of a stratum corneum and has a function that when the medical pressure-sensitive adhesive is applied to a material into which a plasticizer is easily transferred, such as non-plasticized polyvinyl chloride, the adhesive does not damage the material.

The medical bandage of the present invention also has a function that the handling property is very good together with the actions due to the medical pressure-sensitive adhesive of the present invention.

The present invention is explained in more detail by reference to the following examples, but the invention is not limited thereto. In the Examples and the Comparative Examples, all parts, percents, ratios and the like are by weight unless otherwise indicated.

EXAMPLE 1

100 Parts of an acrylic polymer obtained by copolymerizing 10 parts of 2-hydroxyethyl acrylate and 90 parts of 2-ethylhexyl acrylate in a nitrogen gas atmosphere were compounded with 50 parts of sorbitan trioleate and 0.33 part of a trifunctional isocyanate (Colonate L, trade name, made by Nippon Polyurethane Industry Co., Ltd.) as a crosslinking agent in ethyl acetate to obtain a solution of a medical pressure-sensitive adhesive of the present invention.

The solution of the pressure-sensitive adhesive thus obtained was coated on a polyester film and dried to obtain a medical bandage of the present invention having the pressure-sensitive adhesive layer having a thickness of 50 μm.

Comparative Example 1

The same procedure as in Example 1 was followed except that the amount of the crosslinking agent used was changed to 1.33 parts to obtain a medical bandage.

EXAMPLE 2

100 Parts of an acrylic polymer obtained by copolymerizing 5 parts of acrylic acid and 95 parts of 2-ethylhexyl acrylate in a nitrogen gas atmosphere were compounded with 50 parts of octyldodecyl myristate and 0.2 part of a trifunctional isocyanate (Colonate HL, trade name, made by Nippon Polyurethane Industry Co., Ltd.) as a crosslinking agent to obtain a solution of a medical pressure-sensitive adhesive of the present invention.

The solution of the medical pressure-sensitive adhesive thus obtained was coated on a polyester film and dried to obtain a medical bandage having the pressure-sensitive adhesive layer having a thickness of 50 μm.

EXAMPLE 3

The same procedure as in Example 2 was followed except that isocetyl myristate was used in place of octyldodecyl myristate to obtain a medical bandage of the present invention.

Comparative Example 2

The same procedure as in Example 2 was followed except that isotridecyl myristate was used in place of octyldecyl myristate to obtain a medical bandage.

EXAMPLE 4

The same procedure as in Example 2 was followed except that trimethylolpropane triisostearate was used in place of octyldecyl myristate and 0.13 part of a trifunctional isocyanate (Colonate HL, trade name, made by Nippon Polyurethane Industry Co., Ltd.) was compounded as a crosslinking agent to obtain a medical bandage of the present invention.

Comparative Example 3

The same procedure as in Example 4 was followed except that trimethylolpropane 2-ethylhexanoate was used in place of trimethylolpropane triisostearate to obtain a medical bandage.

EXAMPLE 5

The same procedure as in Example 2 was followed except that the amount of sorbitan trioleate used was changed to 80 parts, the amount of the trifunctional isocyanate (Colonate HL, trade name, made by Nippon Polyurethane Co., Ltd.) used as the crosslinking agent was changed to 0.27 part, and 1.6 parts of 2,6-di-tert-butyl-4-methylphenol was used as an antioxidant to obtain a medical bandage.

Comparative Example 4

The same procedure as in Example 5 was followed except that the amount of the crosslinking agent used was changed to 0.11 to obtain a medical bandage.

Comparative Example 5

The same procedure as in Example 5 was followed except that the amount of the crosslinking agent used was changed to 0.47 part to obtain a medical bandage.

EXAMPLE 6

100 Parts of an acrylic copolymer obtained by copolymerizing 5 parts of acrylic acid, 5 parts of N-vinylpyrrolidone, and 90 parts of 2-ethylhexyl acrylate in a nitrogen gas atmosphere were compounded with 50 parts of glyceride trioleate and 0.27 part of aluminum tris(acetylacetonate) as a crosslinking agent in ethyl acetate to obtain a solution of a medical pressure-sensitive adhesive of the present invention.

The solution of the medical pressure-sensitive adhesive thus obtained was coated on a polyester film which had been subjected to a corona discharging treatment and dried to obtain a medical benadage of the present invention having the medical pressure-sensitive adhesive layer with a thickness of 50 μm.

Each of the samples obtained in the Examples and the Comparative Examples described above was stored at 50° C. for 3 days and then subjected to the following tests.

Insoluble Content (Gel Content) in Acrylic Polymer

About 1 g of the pressure-sensitive adhesive of each sample was sampled and the weight ($W_1$) was accurately measured. The same was immersed in ethyl acetate for 3 days and soluble components in the solvent were extracted. The insoluble components were collected and dried, and the weight (W2) thereof was measured. The wt % of the insoluble components was obtained by the following equation:

$$(W_2 \times 100)/(W_1 \times A/B)$$

A=Weight of (acrylic polymer+crosslinking agent)

B=Weight of (acrylic polymer+liquid or pasty component+crosslinking agent+antioxidant).

Adhesion Test

Each sample cut into a width of 12mm was press-adhered to a bakelite plate by reciprocating once a roller having a weight of 2 kg. After 30 minutes since then, the sample was peeled therefrom at an angle of 180° and a rate of 300 mm/minute, and the peeling force at that time was measured.

Skin Adhesion

Each sample was applied to the back of a volunteer and the adhered state after 24 hours since then was visually evaluated. In the evaluation, the sample which was not released or only the circumference of which was released was defined as o and others were defined as x.

Skin Stimulation

The skin stimulation was evaluated by the extent of pain when each sample adhered to the back of the volunteer as above for 24 hours was detached. The skin stimulation of the sample which did not give any feeling of pain at detaching or gave a slight pain (the feeling of which was not serious) was defined as o and the skin stimulation of the sample which gave the feeling of serious pain at detaching was defined as x.

Adhesive Remaining

After detaching the sample adhered to the back of the volunteer as described above for 24 hours, whether or not a part of the pressure-sensitive adhesive remained on the surface of the skin by the cohesive failure was visually evaluated.

Transfer Property

The transfer property of the liquid or pasty component of the pressure-sensitive adhesive into medical fittings or medical instruments was evaluated as follows.

The liquid or plasty component and a polyvinyl chloride were contacted, and the assembly in the contact state was placed in a closed system and was allowed to stand at room temperature for 7 days. The case that it was visually evaluated that the polyvinyl chloride was clearly swelled by the transfer of the liquid or pasty component was defined as x, and other cases were defined as o. The results obtained are shown in the Table below.

TABLE

|  | Gel Content (%) | Adhesive Strength (g/12 mm) | Skin Adhesion | Skin Stimulation | Adhesive Remaining | Transfer Property |
| --- | --- | --- | --- | --- | --- | --- |
| Example 1 | 63.7 | 108 | O | O | O | O |
| Example 2 | 73.3 | 109 | O | O | O | O |
| Example 3 | 74 | 92 | O | O | O | O |

TABLE-continued

|  | Gel Content (%) | Adhesive Strength (g/12 mm) | Skin Adhesion | Skin Stimulation | Adhesive Remaining | Transfer Property |
| --- | --- | --- | --- | --- | --- | --- |
| Example 4 | 48.5 | 237 | O | O | O | O |
| Example 5 | 61.5 | 115 | O | O | O | O |
| Example 6 | 67.4 | 85 | O | O | O | O |
| Comparative Example 1 | 81.7 | 73 | X | O | O | O |
| Comparative Example 2 | 73.2 | 72 | O | O | O | X |
| Comparative Example 3 | 49 | 210 | O | O | O | X |
| Comparative Example 4 | 26.4 | 78 | X | O | X | O |
| Comparative Example 5 | 84.3 | 83 | X | O | O | X |

As is clear from the results shown in the above Table, it can be seen that the samples of the present invention are excellent in all the test items as compared with the samples of the comparative examples.

As described above, the medical pressure-sensitive adhesive of the present invention having the above-described construction has the advantages that the medical pressure-sensitive adhesive has a good skin adhesive property and is safe as showing almost no skin stimulation and giving a very slight damage of a stratum corneum; when the medical pressure-sensitive adhesive is applied to a medical fitting or a medical instrument which uses a material into which a plasticizer is easily transferred, such as non-plasticized polyvinyl chloride, the pressure-sensitive adhesive does not damage the medical fitting or the medical instrument; and further since the liquid or the pasty component in the medical pressure-sensitive adhesive does not transfer into a support, the selective range of the support can be widened.

Further, since the medical pressure-sensitive adhesive is used for the medical bandage of the present invention, the medical bandage of the present invention has the advantages that the medical bandage has a good skin adhesive property and is safe as showing almost no skin stimulation and giving a very slight damage of a stratum corneum at adhering the bandage; when the medical bandage is applied to a material into which a plasticizer is easily transferred, such as non-plasticized polyvinyl chloride, the bandage does not damage the material; and the medical bandage shows a good repeating adhesive property, gives a very less influence on various medical fittings, can be safely and widely used for the medical treatment, and further has a very good handling property.

While the invention has been described in detail and with reference to specific embodiments thereof, it will be apparent to one skilled in the art that various changes and modifications can be made therein without departing from the spirit and scope thereof.

What is claimed is:

1. A medical pressure-sensitive adhesive consisting essentially of 100 parts by weight of an acrylic polymer and from 30 to 100 parts by weight of a liquid or pasty component which is in a liquid state or a pasty state at room temperature and is compatible with the acrylic polymer, wherein the liquid or pasty component comprises at least one ester selected from the group consisting of an ester of a monobasic acid or a polybasic acid each having from 8 to 18 carbon atoms and a branched alcohol having from 14 to 18 carbon atoms and an ester of an unsaturated fatty acid or a branched acid each having from 14 to 18 carbon atoms and a tetrahydric, trihydric or dihydric alcohol, and from 40 to 80% by weight of the acrylic polymer is insolubilized by crosslinking.

2. A medical pressure-sensitive adhesive as claimed in claim 1, wherein said acrylic polymer is a homopolymer of a (meth)acrylic acid ester or a copolymer of the (meth) acrylic acid ester and a monomer copolymerizable therewith.

3. A medical pressure-sensitive adhesive as claimed in claim 2, wherein said (meth)acrylic acid ester has 2 to 15 carbon atoms in the alkyl moiety.

4. A medical pressure-sensitive adhesive as claimed in claim 2, wherein said monomer is at least one member selected from the group consisting of a carboxyl group-containing monomer, a sulfoxyl group-containing monomer, a hydroxyl group-containing monomer, an amido group-containing monomer, an alkylaminoalkyl group-containing monomer, a (meth)acrylic acid alkoxyalkyl ester, an alkoxy group or ether bond at the side chain-containing (meth) acrylic ester, and a vinyl monomer.

5. A medical pressure-sensitive adhesive as claimed in claim 1, wherein the amount of the liquid or pasty component is from 30 to 80 parts by weight per 100 parts by weight of the acrylic polymer.

6. A medical pressure-sensitive adhesive as claimed in claim 1, wherein said ester of the monobasic acid or the polybasic acid and the branched alcohol is at least one member selected from the group consisting of isostearyl laurate, isocetyl myristate, octyldodecyl myristate, isostearyl palmitate, isocetyl stearate, octyldodecyl oleate, diisostearyl adipate, diisocetyl sebacate, trioleyl trimellitate, and triisocetyl trimellitate.

7. A medical bandage comprising a support having formed on at least one surface of the support a layer of a medical pressure-sensitive adhesive, said medical pressure-sensitive adhesive consisting essentially of 100 parts by weight of an acrylic polymer and from 30 to 100 parts by weight of a liquid or pasty component which is in a liquid state or a pasty state at room temperature and is compatible with the acrylic polymer, wherein the liquid or pasty compound comprises at least one ester selected from the group consisting of an ester of a monobasic acid or a polybasic acid each having from 8 to 18 carbon atoms and a branched alcohol having from 14 to 18 carbon atoms and/or an ester composed of an unsaturated fatty acid or a branched acid each having from 14 to 18 carbon atoms and a tetrahydric, trihydric or dihydric alcohol, and from 40 to 80% by weight of the acrylic polymer is insolubilized by crosslinking.

* * * * *